US006126673A

United States Patent [19]
Kim et al.

[11] Patent Number: 6,126,673
[45] Date of Patent: *Oct. 3, 2000

[54] VENA CAVA FILTER

[75] Inventors: Hannah S. Kim, Arlington; David L. Sandock, Littleton; Sepideh H. Nott, Fall River, all of Mass.

[73] Assignee: Boston Scientific Corporation, Natick, Mass.

[ * ] Notice: This patent is subject to a terminal disclaimer.

[21] Appl. No.: 09/195,182

[22] Filed: Nov. 17, 1998

Related U.S. Application Data

[63] Continuation of application No. 08/901,126, Jul. 28, 1997, Pat. No. 5,836,969, which is a continuation of application No. 08/704,843, Aug. 28, 1996, abandoned, which is a continuation of application No. 08/131,203, Oct. 1, 1993, abandoned.

[51] Int. Cl.⁷ .......................... A61B 17/00; A61M 29/00
[52] U.S. Cl. ............................................................. 606/200
[58] Field of Search ........................... 606/1, 108, 191, 606/194, 195, 198, 200; 623/1, 12

[56] References Cited

U.S. PATENT DOCUMENTS

| | | |
|---|---|---|
| 3,540,431 | 11/1970 | Mobin-Uddin . |
| 3,952,747 | 4/1976 | Kimmell, Jr. . |
| 4,425,908 | 1/1984 | Simon . |
| 4,619,246 | 10/1986 | Molgaard-Nielsen et al. . |
| 4,688,553 | 8/1987 | Metals . |
| 4,781,177 | 11/1988 | Lebigot . |
| 4,817,600 | 4/1989 | Herms et al. . |

(List continued on next page.)

FOREIGN PATENT DOCUMENTS

| | | |
|---|---|---|
| 0 448 891 | 10/1989 | European Pat. Off. . |
| 0 348 295 | 12/1989 | European Pat. Off. . |
| 0 430 848 A1 | 6/1991 | European Pat. Off. . |
| 0 437 121 A2 | 7/1991 | European Pat. Off. . |
| 0 462 008 A1 | 12/1991 | European Pat. Off. . |
| 0 472 334 A1 | 2/1992 | European Pat. Off. . |
| 2 587 901 | 4/1987 | France . |
| 8909642 | 7/1989 | France . |
| 9007535 | 6/1990 | France . |
| 2 649 884 | 1/1991 | France . |
| 3417738 | 11/1985 | Germany ............................... 606/200 |
| 835447 | 6/1981 | U.S.S.R. . |
| 1103868 | 7/1983 | U.S.S.R. . |
| 955912 | 2/1988 | U.S.S.R. . |
| 2 200 848 | 8/1988 | United Kingdom . |
| WO 91/04716 | 4/1991 | WIPO . |
| WO 91/11972 | 6/1991 | WIPO . |

OTHER PUBLICATIONS

Kraimps et al., "Conical Endocaval Filters with Metallic Struts: Search for a New Model," Mar. 1992, Ann. Vasc. Surg., 6:99–110.

Kraimps et al., "Optimal Central Trapping (OPCETRA) Vena Caval Filter: Results of Experimental Studies," Nov. 1992, J. of Vasc. and Inter. Rad., 3:697–701.

Herrera et al., Chapter 10—Inferior Vena Cava Filters, Dec. 1991, *Interventional Radiology* (2nd edition), 665–703.

*Primary Examiner*—Michael Buiz
*Assistant Examiner*—William Lewis
*Attorney, Agent, or Firm*—Hoffman & Baron, LLP

[57] ABSTRACT

A vascular filter-comprises an emboli-capturing portion having a set of helical filter-wires joined at a central region and extending in a given direction along the blood vessel in a diverging relationship to the axis of the filter, the wires terminating in free ends constructed to engage the walls of said vessel. A major mid-portion of the length of the free ended wires are of generally helical form, cooperatively related to form an effective emboli capturing array. Anchoring is accomplished by a separate assembly formed of struts and anchoring devices. A parallelogram supporting strut assembly and other members for providing linear engagement with the wall of the vena cava are shown. The parallelogram structure is shown to have filter capability by itself as well.

29 Claims, 10 Drawing Sheets

U.S. PATENT DOCUMENTS

| | | |
|---|---|---|
| 4,830,003 | 5/1989 | Wolff et al. . |
| 4,832,055 | 5/1989 | Palestrant . |
| 4,856,516 | 8/1989 | Hillstead . |
| 4,873,978 | 10/1989 | Ginsburg . |
| 4,943,297 | 7/1990 | Saveliev et al. . |
| 4,954,126 | 9/1990 | Wallsten . |
| 4,957,501 | 9/1990 | Lahille et al. . |
| 4,969,891 | 11/1990 | Gewertz . |
| 4,990,156 | 2/1991 | Lefebvre . |
| 5,059,205 | 10/1991 | El-Nounou et al. . |
| 5,061,275 | 10/1991 | Wallsten et al. . |
| 5,071,407 | 12/1991 | Termin et al. . |
| 5,108,418 | 4/1992 | Lefebvre . |
| 5,108,419 | 4/1992 | Reger et al. . |
| 5,133,733 | 7/1992 | Rasmussen et al. ............... 606/200 |
| 5,135,516 | 8/1992 | Sahatjian et al. . |
| 5,152,777 | 10/1992 | Goldberg et al. . |
| 5,160,342 | 11/1992 | Reger et al. . |
| 5,190,546 | 3/1993 | Jervis . |
| 5,221,261 | 6/1993 | Termin et al. . |
| 5,224,953 | 7/1993 | Morgentaler . |
| 5,300,086 | 4/1994 | Gory et al. . |
| 5,304,121 | 4/1994 | Sahatjian . |
| 5,324,304 | 6/1994 | Rasmussen . |
| 5,329,942 | 7/1994 | Gunther et al. . |
| 5,344,427 | 9/1994 | Cottenceau et al. ............... 606/200 |
| 5,370,657 | 12/1994 | Irie . |
| 5,375,612 | 12/1994 | Cottenceau et al. . |
| 5,382,261 | 1/1995 | Palmaz . |
| 5,405,377 | 4/1995 | Cragg . |
| 5,476,508 | 12/1995 | Amstrup . |
| 5,836,969 | 11/1998 | Kim et al. ............... 606/200 |

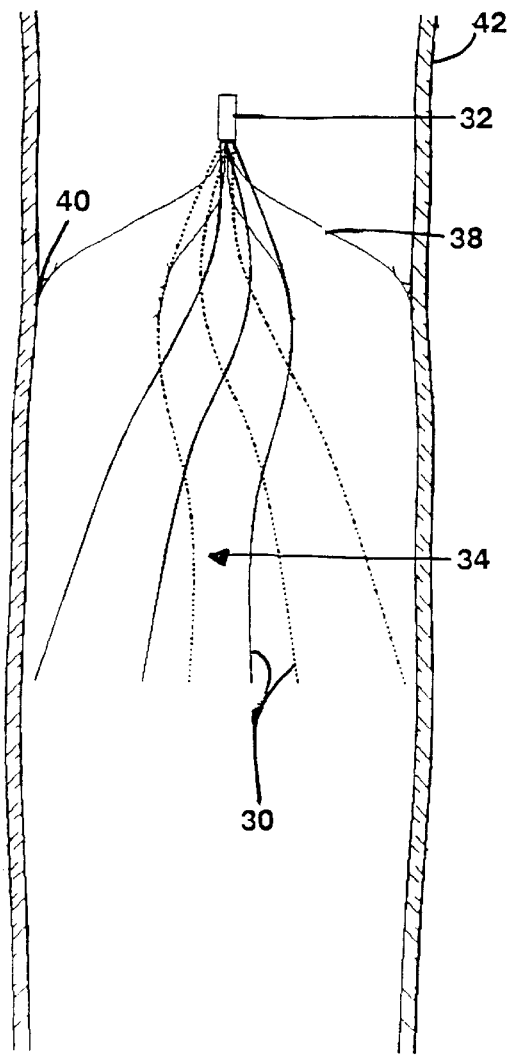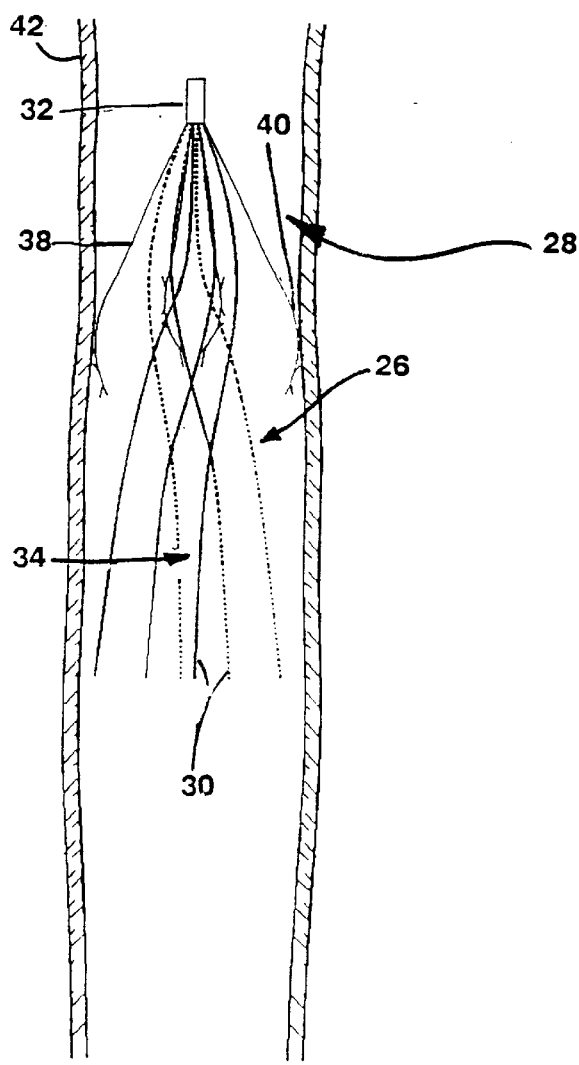
FIG. 4  FIG. 4b
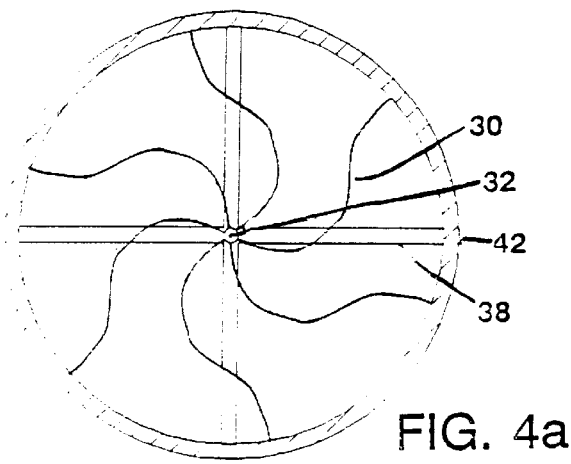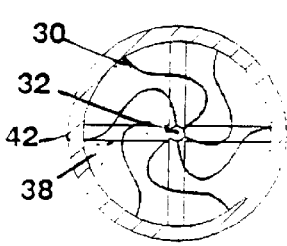
FIG. 4a  FIG. 4c

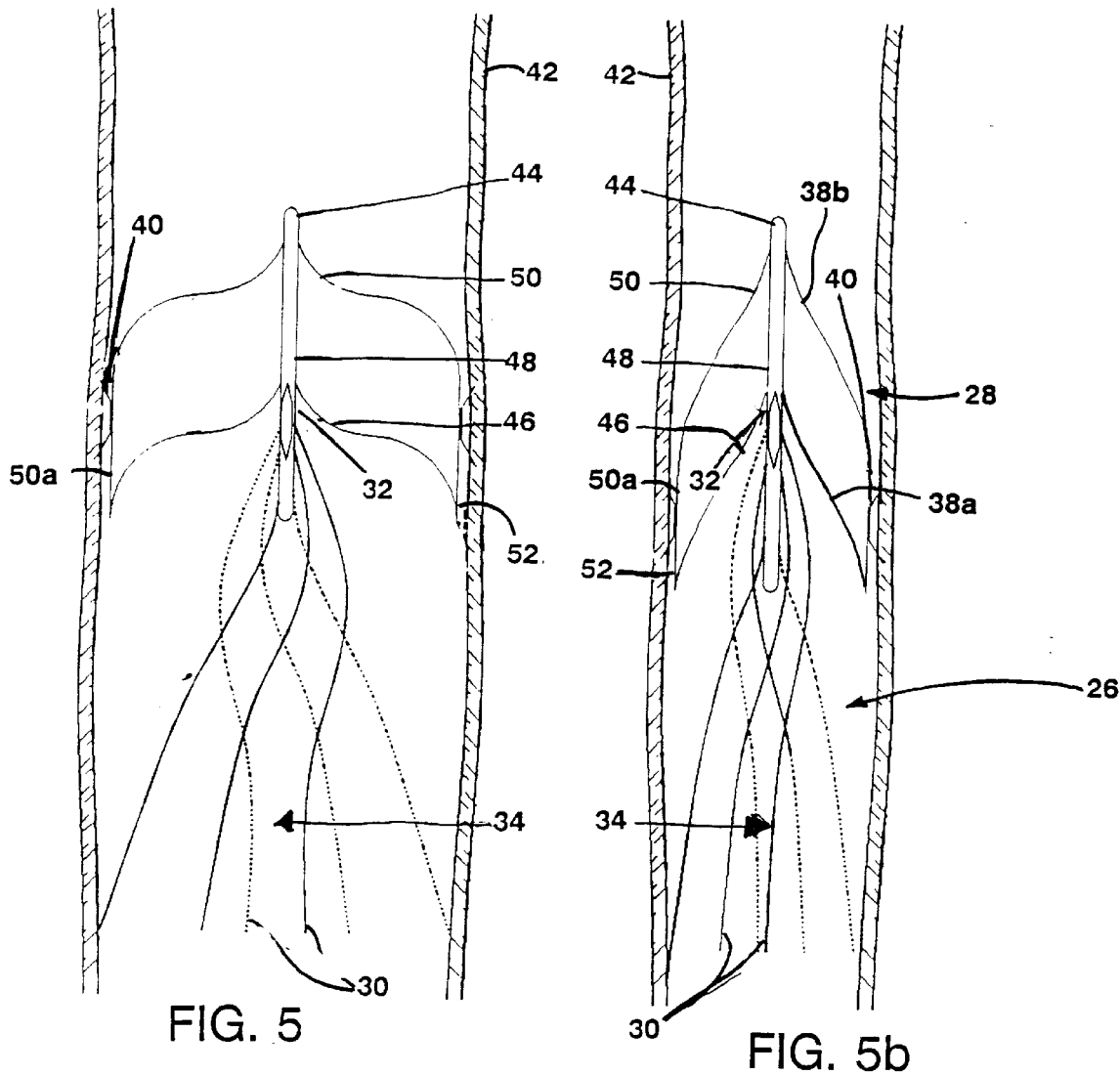
FIG. 5
FIG. 5b
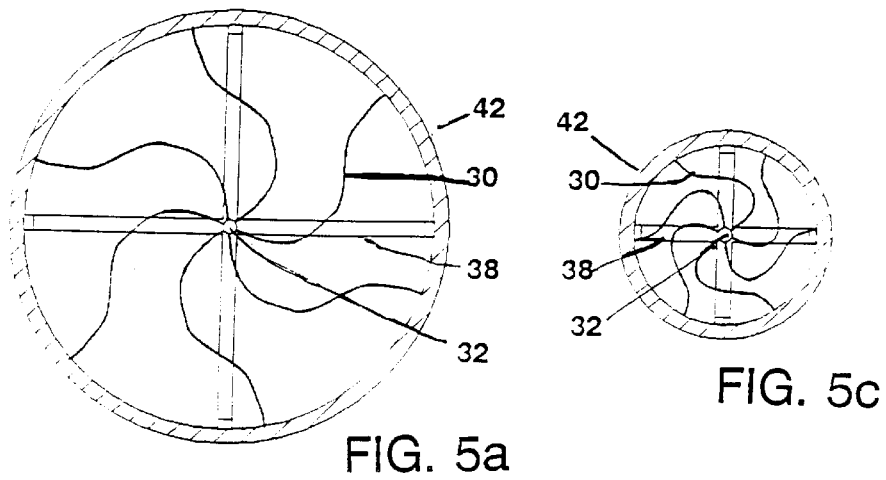
FIG. 5a
FIG. 5c

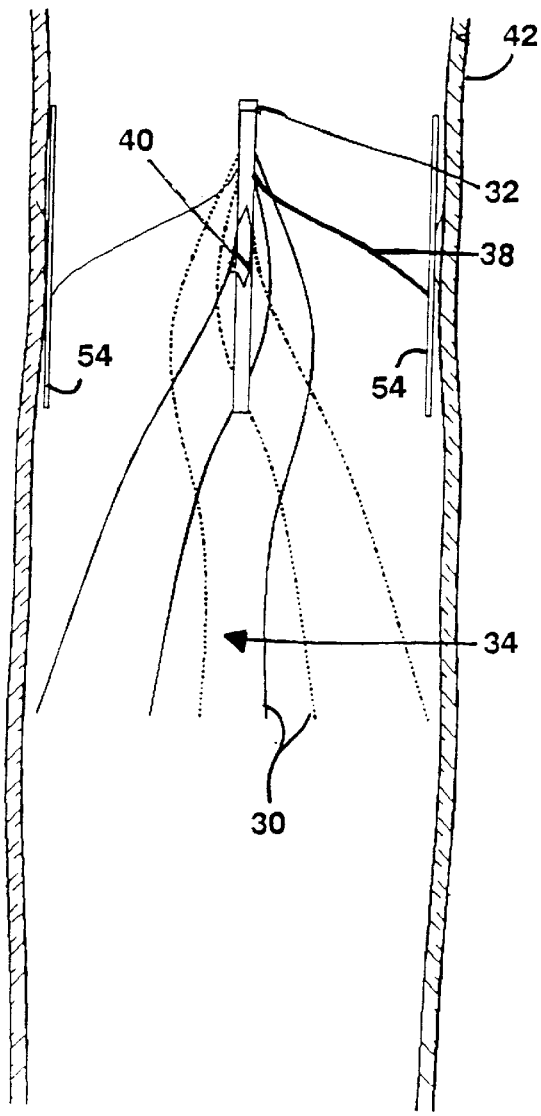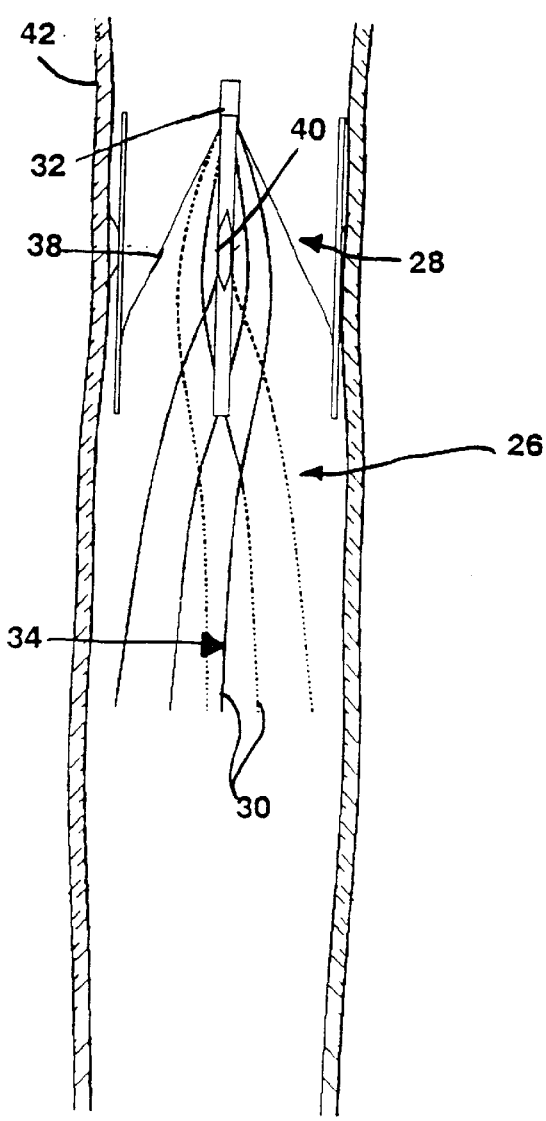
FIG. 7
FIG. 7b
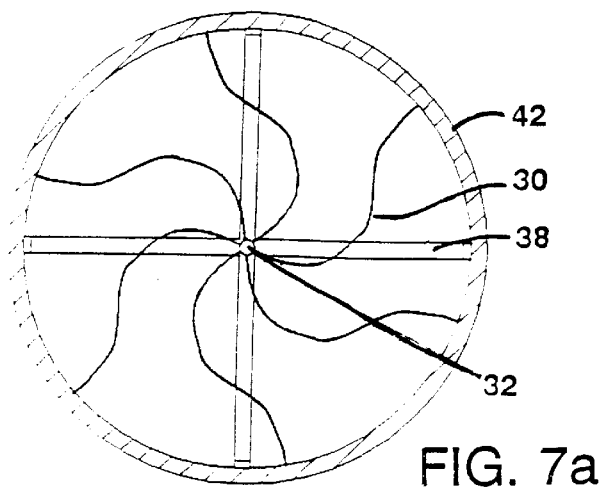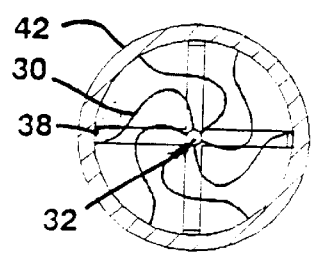
FIG. 7a
FIG. 7c

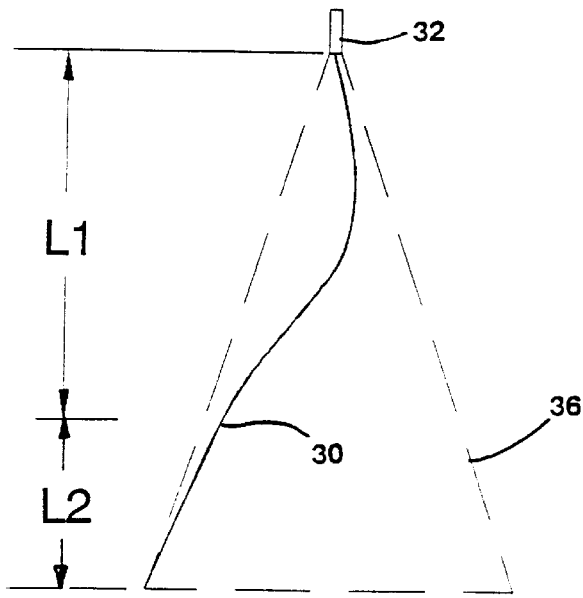
FIG. 10
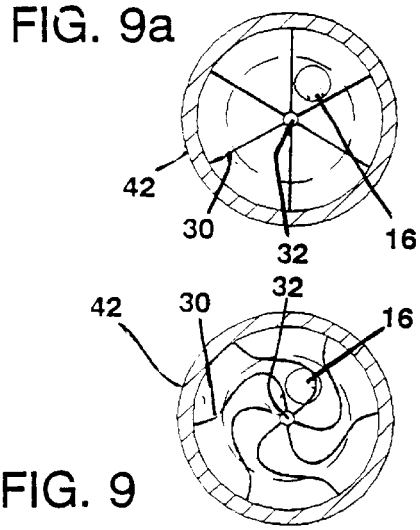
FIG. 9a
FIG. 9
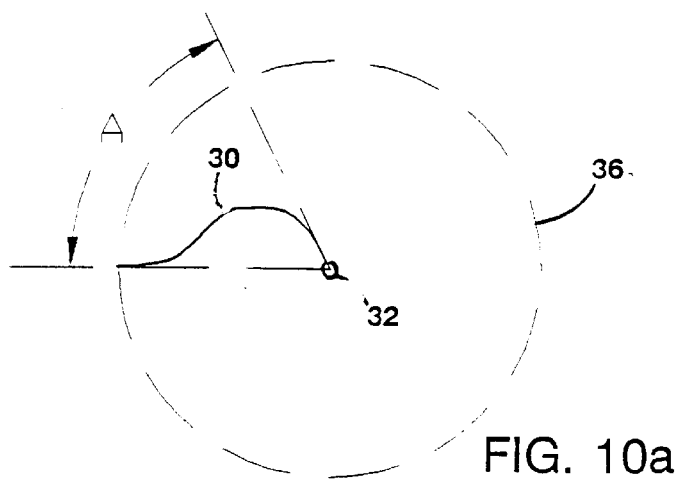
FIG. 10a

FIG. 11 FIG. 13 FIG. 15
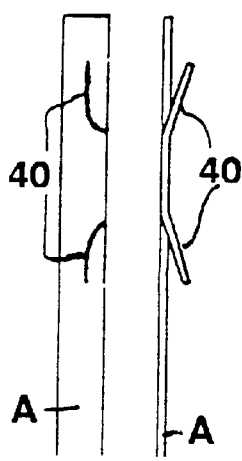
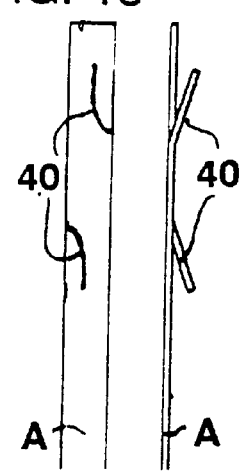
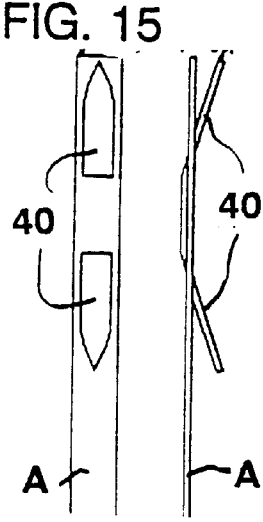
FIG. 12 FIG. 14 FIG. 16
FIG. 17 FIG. 19 FIG. 21
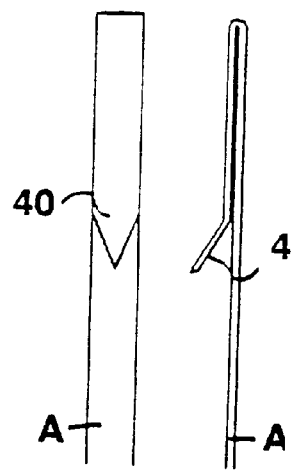
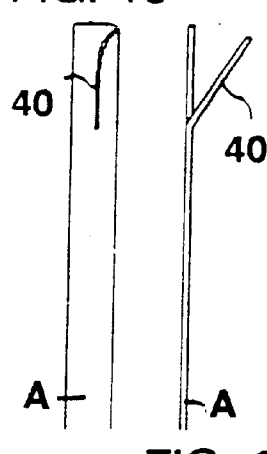
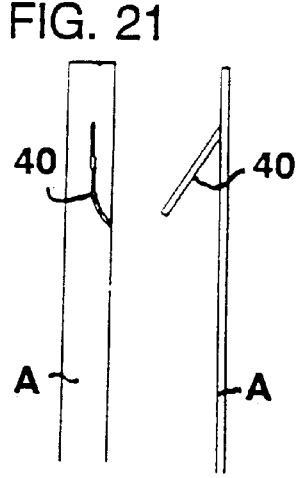
FIG. 18 FIG. 20 FIG. 22
FIG. 23 FIG. 24
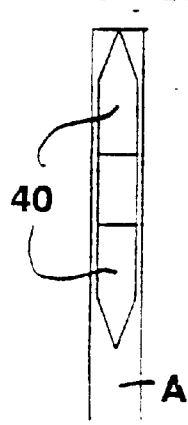

VENA CAVA FILTER

This application is a continuation of U.S. application Ser. No. 08/901,126, filed Jul. 28,1997, issued on Nov. 17, 1998 as U.S. Pat. No. 5,836,969, which is a continuation of U.S. application Ser. No. 08/704,843, filed Aug. 28, 1996, abandoned, which is a continuation of U.S. application Ser. No. 08/131,203, filed Oct. 1, 1993, abandoned.

This invention relates to blood filters, and more particularly to filters designed to be implanted in a human vena cava and the like.

BACKGROUND OF THE INVENTION

Vena cava filters are designed to capture emboli and prevent them from migrating via the blood stream into the pulmonary arteries. A vena cava filter is typically placed via a catheter inserted through a puncture in a vein. For insertion, the filter is collapsed within the catheter and is released after the catheter has accessed the vena cava.

Known vena cava filters in collapsed form have required relatively large diameter catheters and correspondingly large puncture openings which has limited the access point generally to the largest veins, i.e. the femoral and jugular veins. The relatively large puncture wound has at times produced complications.

SUMMARY OF THE INVENTION

The present invention provides filters of small collapsed construction that are self-centering in the human vena cava over the considerable range of diameters of vena cava that exist. The invention also provides a high degree of consistency and repeatability in placement of the filter and secure anchoring of the filter to the vein wall to ensure no movement, particularly during the acute phase, until tissue growth over the anchors occurs to make the filter more secure.

The invention has various aspects which individually contribute improvement, and which, in select combinations, enable a smaller collapsed form and improved performance to be achieved.

Specifically, in one important respect, a vena cava filter is provided which, by separation of the filtering and anchoring functions into two or more sets of legs or struts, enables small diameter collapse of each set, in a construction which is desirably short and in which the axially spaced wall contact of the sets achieves self-centering over a wide range of vena cava sizes. Secure anchoring is also achieved at a precise location against movement in either direction as a result of firm engagement of the anchoring devices.

According to one principle of the invention, a set of filter-wires is provided, which is to achieve the clot capturing function, capable of being deployed over a wide range of cone angles dependent upon the size of the vena cava. These filter-wires extend generally upstream from a central region of connection, to wall-engaging free ends. The filter-wires of the set desirably have a general helical matching configuration that presents an effective clot-capturing aspect, in a construction that is readily collapsible into a small compass. From the axis also extends a collapsible strut structure which supports wall-engaging anchors or projections that securely engage the vessel wall at a location or locations spaced axially from the region of contact of the free ends of the filter-wires. Because nearly all of the filtering action is accomplished by the set of helical filter-wires, the design of the strut structure need not deal with its filtering aspect. While other cross-sections are operable in certain circumstances, the struts are preferably of rectangular transverse cross-section, i.e., of strip form, the long dimension of this cross-section arranged circumferentially, and the struts extend at, effectively, a steeper angle relative to the longitudinal axis than do filter-wires. This steepness favorably affects their force-applying capability at the vena cava wall. Other strut cross-sections including oval and even circular can, however, be employed under certain circumstances.

The strut structures in certain preferred embodiments diverge to their wall-contacting points in the opposite axial direction to that of the filter-wires in order to achieve the self-centering effect. Because of the strip-form construction they can readily support multiple anchors or projections along their respective lengths in the outer regions to provide firm anchoring capability in both small and large vena cava. In another preferred form, the strut structure extends in the same axial direction as does the filter wire structure, but at a steeper effective angle to achieve firm anchoring at a location spaced axially from the wall contact region of the filter-wires. Again this structure achieves a secure self-centering function over a wide range of vena cava sizes. The self-centering performance of preferred embodiments is assisted by employment of linear axially parallel wall-engaging elements supported by the strut structure. These are particularly beneficial in embodiments in which the strut structure diverges in the same direction as the filter-wires, but also have applications in a "ski-like" single support point configuration in which the strut structure diverges in the opposite direction from that of the set of filter-wires.

A parallelogram-like strut support of opposite ends of linear wall-engaging elements is an important feature in certain preferred embodiments. It enables the linear wall elements to maintain their parallel relationship to the axis of the filter, thus centering the filter over a range of sizes. This novel parallelogram support, while contributing significantly to the performance capability in combination with one of more sets of helical filter-wires, also has merit in its own right in which the support struts are constructed and arranged themselves to have a filtering function, or in which such strut structure is combined with other filtering arrays.

While presently preferred to be constructed of elastic metals such as nickel titanium alloy operating in the linear portion of the stress/strain curve, other materials can be used to advantage. Other materials of metallic or polymeric nature, including super-elastic metal, shape memory metal, and newly developing materials, may be used to advantage. Surface treatments of the filter-wires and supports can contribute to their effectiveness. Following the concepts provided herein, it becomes possible to form vena cava filters sufficiently small that in certain cases they may be introduced less invasively through smaller veins when access to the femoral or jugular vein is not possible.

These and other objects and features of the invention will be understood from the following summary of certain specific features of the invention and from the detailed description of presently preferred embodiments in connection with the drawings.

According to one aspect of the invention, there is provided a vascular filter for placement in a blood vessel for preventing the movement of emboli in the blood stream of a human. The filter includes a set of filter-wires that diverge from a central region in a given direction along the blood vessel forming an emboli-capturing array, the filter-wires having portions that engage the vessel wall, and an anchoring assembly defined by at least one set of struts joined centrally with said set of filter-wires. Portions of the anchoring assembly are constructed and arranged to engage the wall of the blood vessel in a manner anchoring the filter in position, the region of the anchoring being spaced from the region of contact of the set of filter wires with said vessel wall.

In preferred embodiments, the anchoring assembly includes anchoring formations supported by the struts and disposed for engagement with the walls of the blood vessel, each of the formations comprising at least one pointed projection to engage wall tissue and anchor the strut thereto.

In certain preferred embodiments each anchoring formation comprises at least a pair of pointed projections, the projections of the pair being oriented in opposite directions along the blood vessel, each being angled to penetrate wall tissue, the pair being effective in resisting dislodgement of the strut in either direction along the vessel. Also, in preferred embodiments the wall-engaging formations supported by the struts are constructed and arranged to maintain generally linear contact with the vessel walls.

In preferred embodiments of this aspect of the invention the filter-wires of the set are helically configured and arranged to form an effective clot-capturing array that can be radially expanded and contracted to adapt to vessels of different sizes.

According to another aspect of the invention, there is provided a vascular filter for placement in blood vessels for preventing the movement of emboli in the blood stream of a human, the filter comprising an emboli-capturing portion having a set of filter-wires joined at a central region and extending in a given direction along the blood vessel, and terminating in free ends constructed to engage the wall of the vessel, the wires having a diverging relationship to the axis of the filter. The filter features at least a major mid-portion of the length of the free ended wires of the set being of generally helical form, cooperatively related to form an effective emboli-capturing array.

Preferred embodiments of these aspects of the invention have one or more of the following features.

The filter-wires have substantially less transverse cross-section and are collapsible into a small size bundle. The filter wires are comprised of elastic metal of round cross-section, their helical extent being curved at a radius of the order of ¼ inch to ½ inch and the struts are comprised of flat strip-form material arranged with the direction of thickness of the strip oriented radially.

The filter wires are comprised of elastic material, the wires being cooperatively related, upon compaction, to elastically straighten and to meet closely with each other, enabling into a small size, and enabling radial compaction of the set into an introducer catheter of about 9 French or less outer diameter for insertion into a blood vessel. The wires when released from the catheter into the blood vessel are constructed to expand to form the effective emboli-capturing array.

The filter is constructed for placement in blood vessels over a range of sizes, portions of the filter-wires adjacent the free ends being relatively straight, enabling, substantially end-contact of the wires with the walls of the blood vessel over the range of vessel sizes.

Preferably, all of the filter-wires are curved in the same general helical direction. Alternatively, the wires of the set of filter-wires may comprise multiple subsets, the wires of one set being curved in the opposite helical direction from the helical direction of curvature of wires of another subset.

For anchoring the filter, an anchoring assembly provides anchoring formations distributed about the filter. The anchoring formations are provided with parallelogram-like supports arranged to adapt to the walls of vessels over a range of sizes while maintaining substantially the same attitude with respect to the walls of the vessel. Preferably the parallelogram-like supports are constructed and arranged to expand from a collapsed condition without change in the overall length of the filter.

In certain preferred embodiments of above mentioned aspects of the invention the struts diverge from the central region in a direction opposite to the direction of divergence of the filter-wires, the struts terminating in portions that engage the wall of the blood vessel, with the spacing of the regions of contact of the filter-wires and struts with the vascular wall being selected to stabilize the filter in the vessel in a generally centered relationship. In such embodiments, preferably the wall-engaging formations supported by the struts are constructed and arranged to maintain generally linear contact with the vessel walls, preferably the wall-engaging formations being linear elements each supported in its mid-region by a strut of the set.

In other preferred embodiments, the struts are short relative to the filter-wires and diverge in the same direction as the filter-wires, but at a greater angle relative to the longitudinal axis of the filter. The spacing of the regions of contact of the filter-wires and struts with the vascular wall are selected to stabilize the filter in the vessel in a generally centered relationship.

In such embodiments, preferably the outer, wall-engaging formations supported by the struts are constructed and arranged to maintain generally linear contact with the vessel walls, the wall-engaging formations being linear elements each supported in its mid-region by a strut of the set.

In preferred embodiments, wall-engaging formations are linear elements, the linear elements being supported at one end by a strut of the set, and the other end of each of the linear elements is joined to and supported by a respective strut of a second set of struts of the assembly, each of the linear elements comprising an integral extension of at least one of the respective supporting struts. Preferably, the struts of the second set are centrally joined to each other at a location spaced axially from the region at which the struts of first set are joined, providing effectively parallelogram-like support to the linear wall-engaging elements to assure substantially linear contact with the vessel wall over a range of sizes of the vessel.

In other preferred embodiments, the struts have free end portions constructed to engage the wall of the vessel, there being a plurality of anchoring formations on the strut. The formations are arranged so that one formation is relatively more effective for anchoring in walls of blood vessels of relatively large size and the other formation is relatively more effective for anchoring in walls of smaller size vessels.

Preferably, the anchoring formations comprise at least one pointed projection. In certain preferred embodiments, each anchoring formation comprises at least a pair of pointed projections, the projections of the pair being oriented in opposite directions along the blood vessel, each being angled to penetrate wall tissue and effective in resisting dislodgement of the strut in either direction along the vessel.

In certain embodiments, preferably the filter wires are of round cross-section and the struts are of rectangular transverse cross-section, the thin dimension of the strut cross-section being arranged in the radial direction.

In certain embodiments, preferably a surface treatment is included on the struts and/or wires that enhances their effectiveness. In certain embodiments the treatment is a biocompatible polymeric coating and in other embodiments it is a metal coating.

In one particular aspect of the invention there is provided a vascular filter for placement in blood vessels for preventing the movement of emboli in the blood stream of a human, the filter including an anchoring assembly comprising anchoring formations distributed about the filter and mounted on parallelogram-like supports arranged to adapt to the walls of vessels over a range of sizes.

Preferred embodiments of this aspect of the invention may have the following features.

The parallelogram supports themselves form at least part of an emboli-capturing array. The outer wall-engaging elements are constructed and arranged to make generally linear contact with the vessel wall, one end of each of the wall-engaging elements being joined to and supported by a strut of a first set of struts, and the other end of each of the wall-engaging elements being joined to and supported by a respective strut of a second set of struts. The second set of struts are centrally joined to each other at a location spaced axially from the region at which the first set of struts are joined, providing effectively parallelogram-like support to the outer, linear wall-engaging elements. Preferably each of the linear wall-engaging elements comprises an integral extension of at least one on the respective supporting struts.

BRIEF DESCRIPTION OF DRAWINGS

FIGS. 2–8 are side views of respective preferred embodiments of the invention implanted in vena cavae.

FIGS. 2a–8a are transverse views, respectively, looking in the direction of the longitudinal axis of the embodiments of FIGS. 2–8.

FIGS. 2b–8b are side views, respectively of the embodiments of FIGS. 2–8 implanted in vena cavae having smaller diameters than those shown in FIGS. 2–8.

FIGS. 2c–8c are transverse views respectively looking in the direction of the longitudinal axis of the embodiments of FIGS. 2b–8b.

FIGS. 9 and 9a show, for comparison, transverse views in the direction of flow of filters having helical and straight wires interacting with emboli 16 travelling in vena cavae.

FIG. 10 is a two-dimensional side view of a filter wire which has a straight end-portion and a curved portion.

FIG. 10a is an end view of the filter wire shown in FIG. 10.

FIG. 11 is a, front view of an end portion of a strut showing a preferred pointed projection design.

FIG. 12 is a side view of the pointed projection design of FIG. 11.

FIGS. 13 and 14, 15 and 16, 17 and 18, 19 and 20, 21 and 22, and 23 and 24 are pairs of views similar to FIGS. 11 and 12, respectively illustrating alternative pointed projection embodiments.

DESCRIPTION OF PRESENTLY PREFERRED EMBODIMENTS

Figure 1:
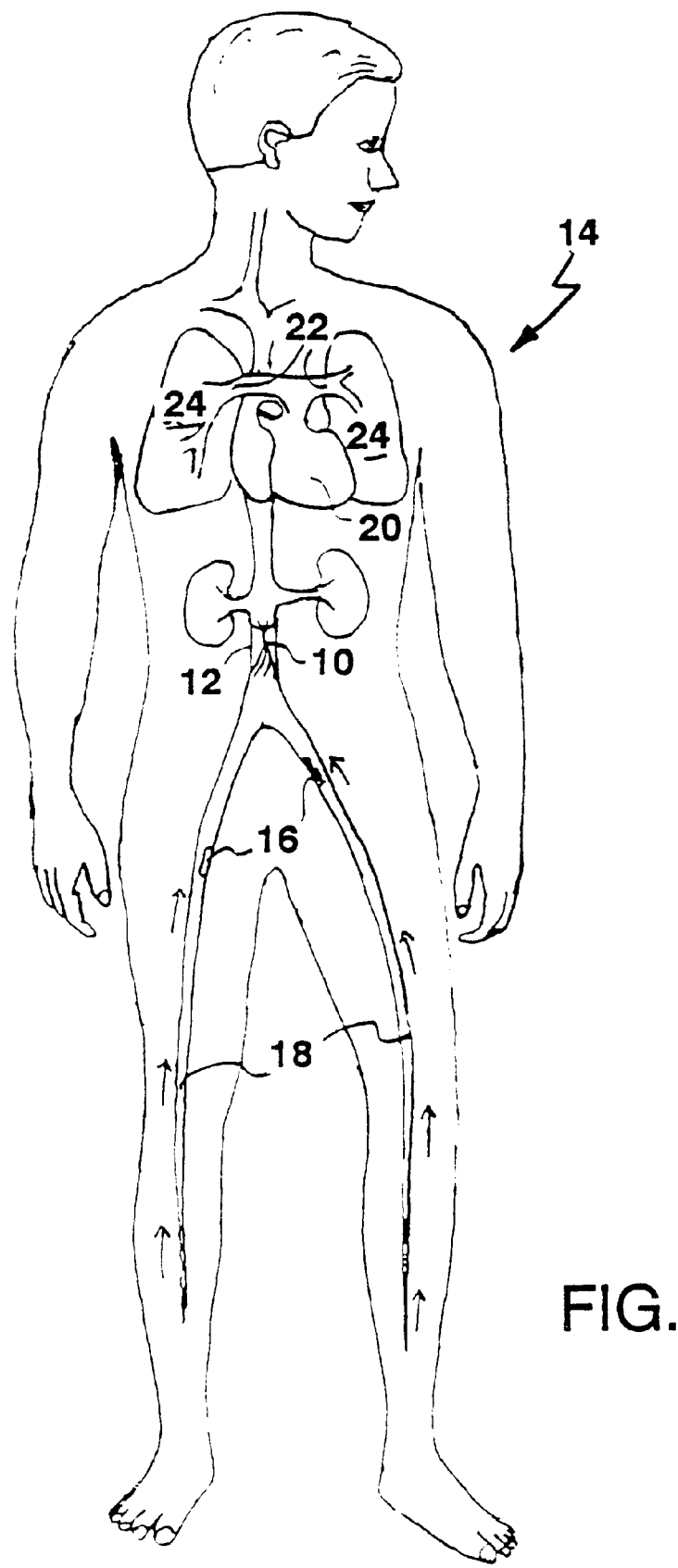
FIG. 1 is a front view, partially cut away, of a human with a preferred embodiment of the invention in place.

As shown in FIG. 1, vena cave filter 10 is implanted in the inferior vena cava 12 of human 14, and is designed to capture emboli 16 formed in the leg veins 18. If vena cava filter 10 is not implanted, emboli 16 may be transported by blood flowing through the veins, (arrows represent direction of blood flow) through heart 20, and into the pulmonary arteries 22. Because pulmonary arteries 22 have smaller diameters than vena cava 12, an embolus 16 may become lodged and restrict the blood flow to one of lungs 24. This may result in the body's oxygen supply being partially or wholly cut off and may possibly result in death.

Referring now generally to FIGS. 2–7, preferred vena cava filter embodiments each respectively include an emboli capturing portion 26 and an anchoring portion 28. Emboli capturing portion 26 is comprised of a set of filter-wires 30 which are joined at common apex 32 and extend in a diverging manner in a given direction to conform to an imaginary cone surface 36 (shown as the dashed lines in FIG. 10).

Emboli capturing portion 26 is comprised of filter-wires 30 extending in a helical fashion to form spirals when viewed axially. This shape will cause an embolism to be channeled into central apex region 34 of the filter. Because the filter is placed concentrically in the vena cava, the filter will hold the trapped embolism near the center of the vena cava where the blood flows fastest. It is important to trap the embolism in a current of fast moving blood to allow the body's natural lysing process to efficiently dissolve the embolism. Cross-sectional views of filters employed in different size vena cavae are shown in FIGS. 2a–8a and FIGS. 2c–8c. The apparent curvature of the filter-wires is greater in the smaller diameter case (FIGS. 2c–8c) because of compaction of the emboli capturing array.

FIGS. 9 and 9a show that a helical filter-wire pattern (FIG. 9) provides a greater capturing aspect for emboli 16 travelling in the vena cava than does a straight wire arrangement (FIG. 9a). Thus, the spiral shape of the wires allows favorable interaction between emboli and filter-wires, resulting in favorable emboli capture without significant impedance of blood flow.

At the same time, the helical shape of filter-wires 30 further facilitates implantation with small catheters because the curvature of the wires may be straightened to a great extent without causing the wire to undergo permanent deformation, thus enabling collapse of the structure into a small package for insertion.

It is presently preferred that filter-wires 30 all spiral in a single direction, as shown in FIGS. 2, 4, 5, 6 and 7. Effective emboli-capturing array can be achieved with relatively few wires and the structures made of fine wires can be collapsed to fit inside a small introducer catheter, e.g., of 9 French outer diameter. Filters shown in FIG. 3, with filter-wires 30 spiraling in opposite directions may, however, be employed in certain circumstances.

In preferred embodiments, the mid-portions of the individual filter-wires are helically curved while outer portions are less curved or even completely straight. The straight and curved portions of such an individual filter-wire 30 extending from apex 32 are shown in FIGS. 10 and 10a. In the preferred embodiment, the initial portion of the filter-wire near the apex (shown as the initial segment of L1 in FIG. 10a) is also approximately straight. The mid-portion (the middle segment of L1) is curved with an approximate angle of 30 degrees relative to the longitudinal axis of the cone 36, and the outer end-portion (L2) is again straight. The straight outer end-portion prevents the outer tip of filter-wires 30 of an inserted device from bending inward toward the center of the vena cava and potentially impeding blood flow when the filter is inserted in very small lumens.

Adequate emboli capturability is achievable in single direction helical filters by using six filter-wires, and in double spiral filters by using eight filter-wires. Filter-wires 30 are preferably formed from nickel titanium alloy, although titanium, titanium alloy, stainless steel, or any other biocompatible material with elasticity may in certain circumstances be employed to advantage. In the preferred cases of use of nickel titanium alloy, the wires are operating in the linear portion of the stress/strain curve of the alloy, though it is possible to employ wires operating in the super-elastic region while obtaining benefits of the invention. Likewise, thermally responsive shape-memory metal can be employed with the geometric and spatial constraints provided by the invention. It is also anticipated that new materials, as they are developed, will be useful. Coatings, such as biocompatible polymeric coatings, and surface treatments, such as metallization with a noble metal can be applied to the wires and struts to advantage.

We have found that the diameter of the helical wires can be determined by two considerations: the wires must be stiff enough to retain the generally, helical and conical shape, and must be small enough to collapse to fit within the desirably small introduction catheter. The presently preferred filter-wire diameter is between 0.008 and 0.020 inch, and preferably between 0.012 and 0.016 inch. While in presently preferred embodiments the wires are of round cross-section, other shapes are also-functional.

Figure 2:
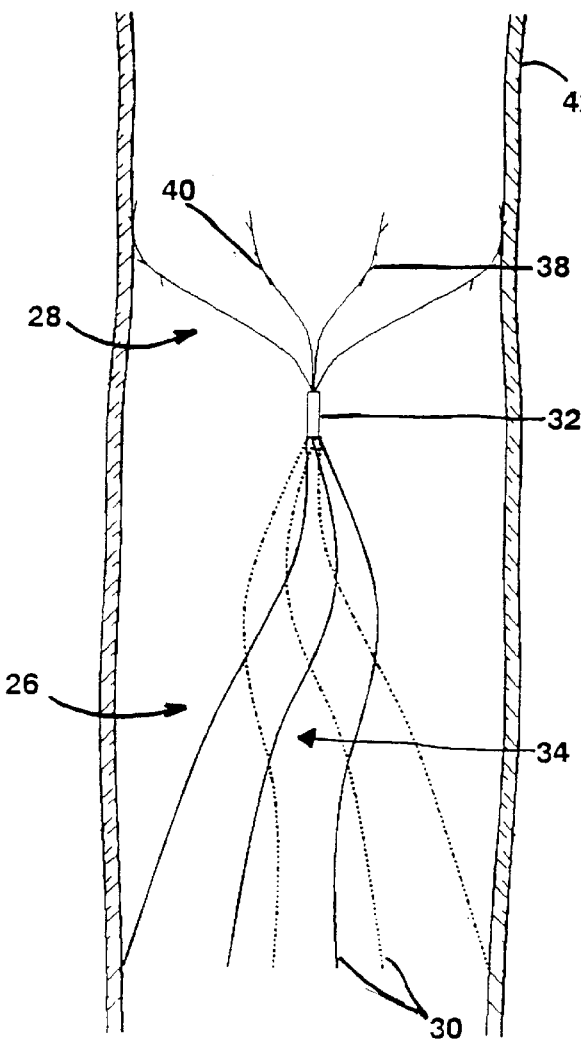
Figure 3:
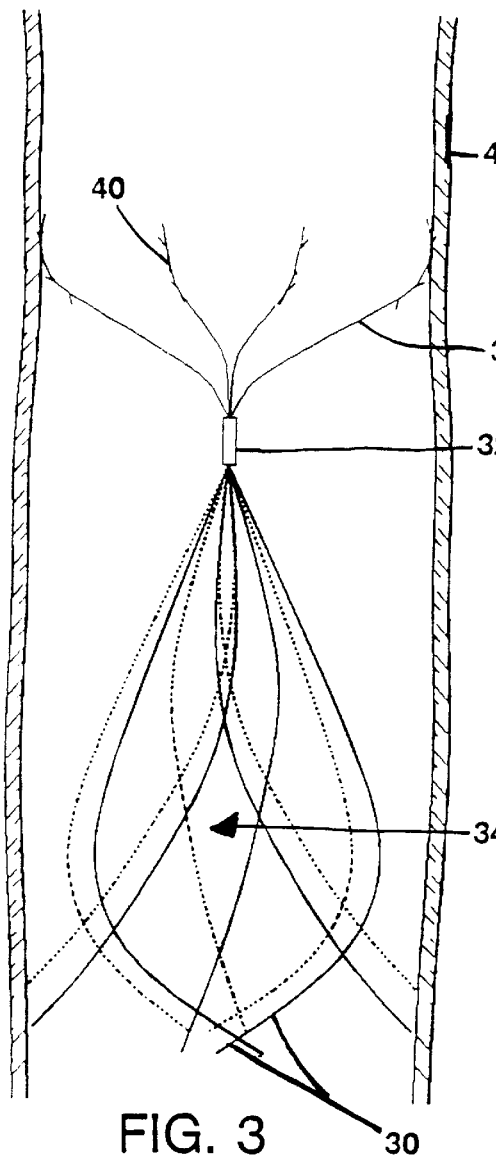
Figure 3B:
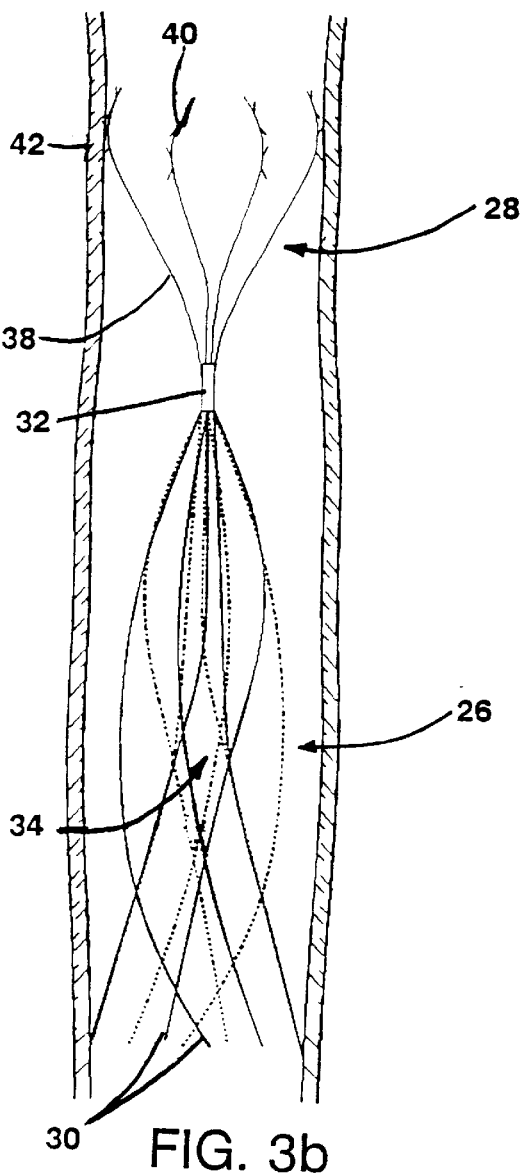
Figure 3A:
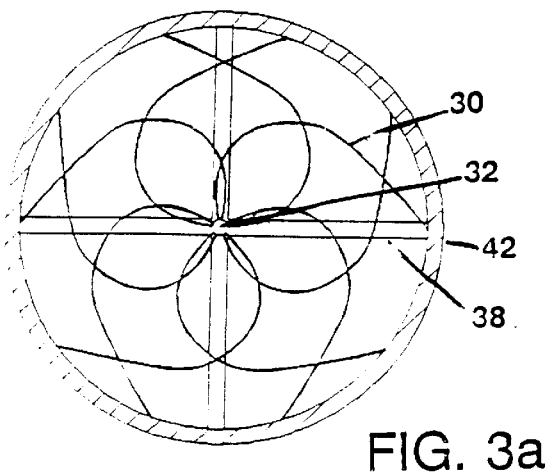
Figure 3C:
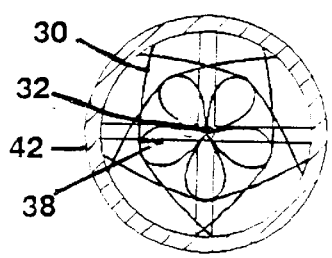
Figure 6:
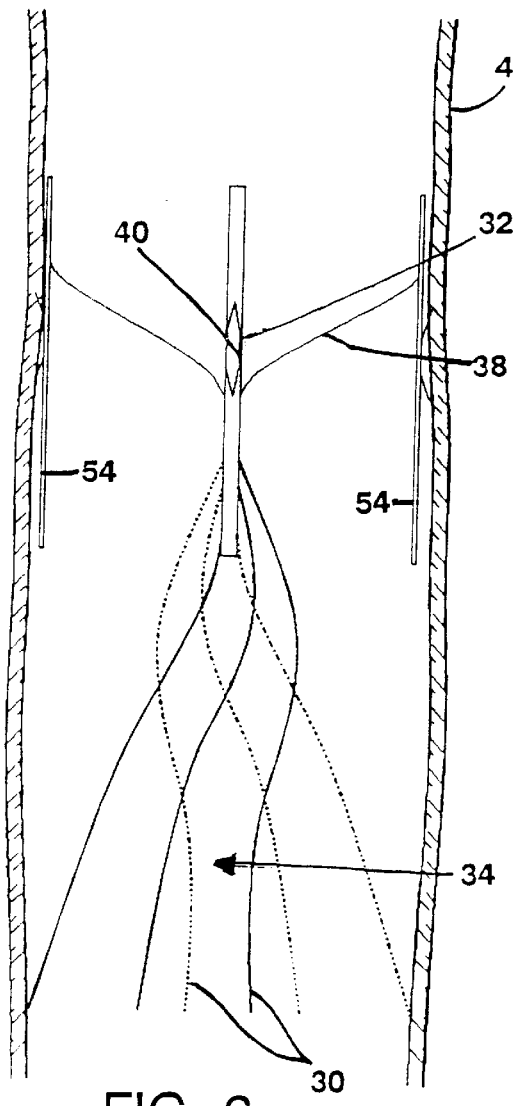
Figure 6B:
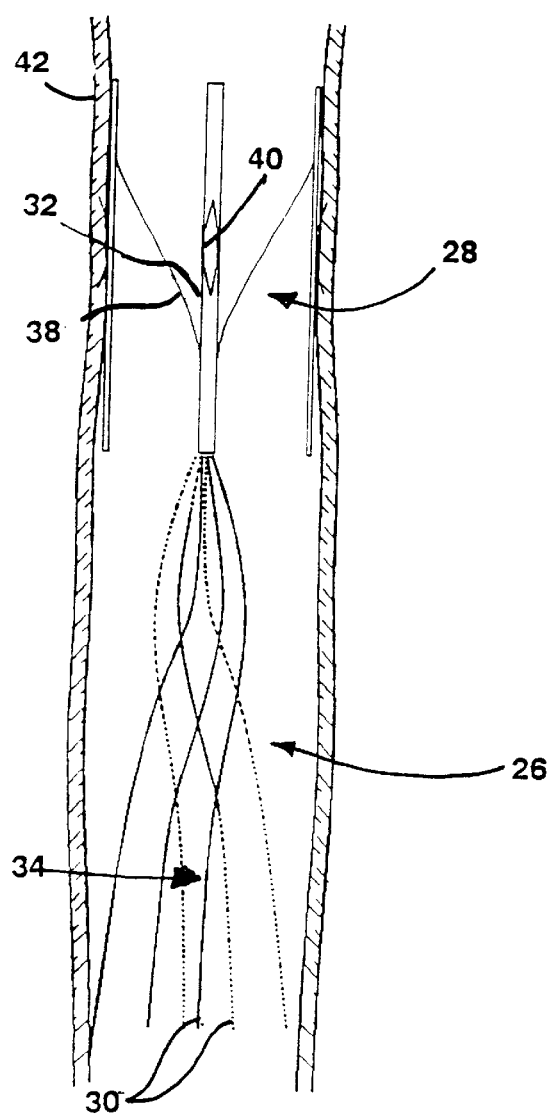
Figure 6A:
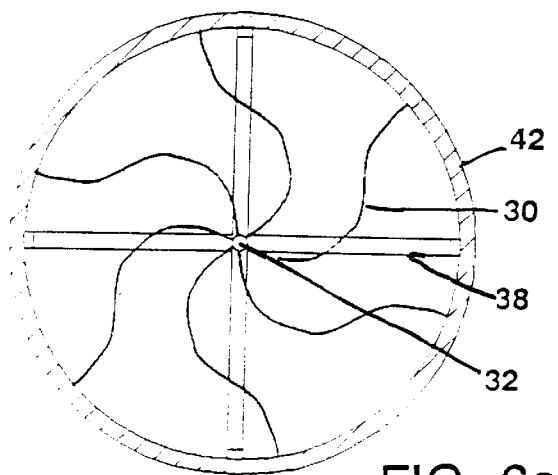
Figure 6C:
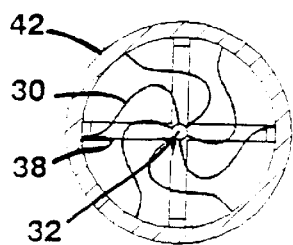

Anchoring portion 28 is comprised of a set of struts 38 which are joined at common-apex 32 and extend in a diverging manner in a given direction. In FIGS. 2, 3 and 6 the anchoring portion extends in a direction opposite to the filter-wires extension, while in FIGS. 4, 5 and 7 the anchoring assembly and filter-wires extend in the same direction, each construction having certain important advantages. As will be discussed more fully below with reference to FIGS. 11–24, pointed projections 40 are preferably disposed on struts 38 to engage the vena cava wall 42 and hold the filter in place.

The struts or devices to engage them to the lumen wall form a ring of contact points or regions which is of generally the same diameter as, and spaced axially from, the ring of contact points between the filter-wires and the tissue.

The struts 38 thus act to resist tilting and center the vena cava filter and also to hold it in place so that it will not migrate toward the heart or legs. The ability of the vena cava filter to self-center upon insertion enables highly effective filter performance over a wide range of lumen configurations and placement techniques.

To adequately hold the filter in place, struts 38 exert a radial force normal to the vena cava walls. Struts 38 are also sufficiently resilient to be compressed into the introducer catheter and to regain their original shape after being released. In presently preferred embodiments, wire having a rectangular or strip cross-section is employed, though oval-shaped or round cross-sections can also be employed. In the case of rectangular or oval cross-section, the wire is preferably oriented so that the long dimension is parallel with and adjacent to the vena cava wall, with the narrow direction arranged radially. The thickness of the strut wire preferably is between 0.003 and 0.015 inch and more preferably between 0.005 and 0.009 inch. The width of the strut wire preferably is between 0.020 and 0.045 inch and more preferably between 0.025 and 0.035 inch.

Strut wire may be made of the same material as the filter-wires, such as nickel titanium alloy, titanium, titanium alloy or stainless steel, or any other biocompatible material having appropriate physical properties.

Strut wires 38 in the embodiments shown in FIGS. 2–4 preferably are shorter than filter-wires 30 because there is a limited amount of space inside inferior vena cava 12 to implant the filter 10. Additionally, the use of short strut wires provides greater stability to the filter because a greater radial force may be delivered to the vena cava wall.

Figure 2B:
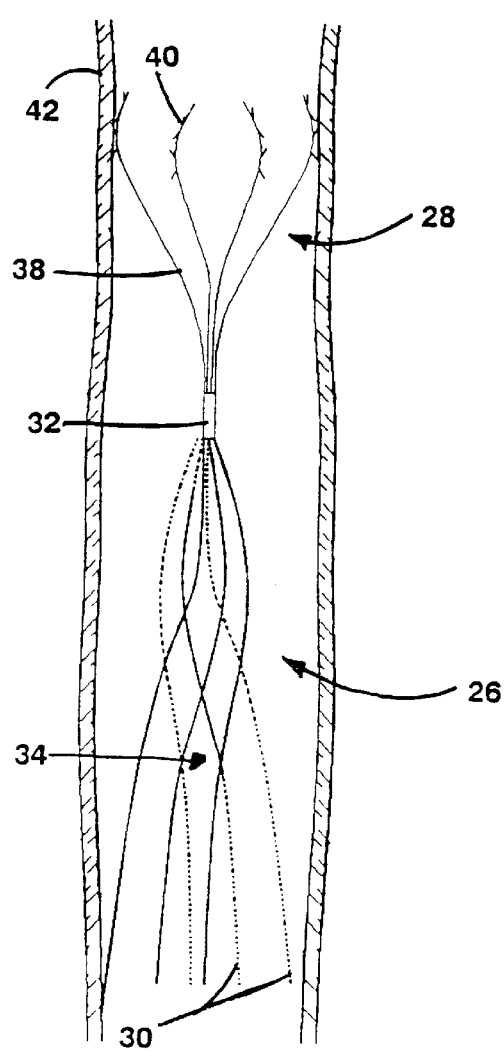
Figure 2A:
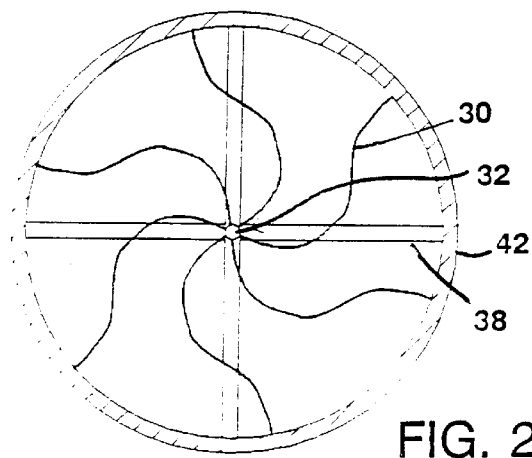
Figure 2C:
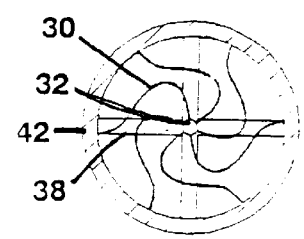

The length of contact between the strut wire 38 and the vena cava wall 42 may depend on the vena cava diameter. FIGS. 2 and 2b illustrate how multiple pointed projections can be utilized to maintain contact with the vena cava wall in various diameter vessels.

As shown in FIG. 5, in a preferred embodiment, anchoring portion 28 is comprised of two sets of struts 38a and 38b which are joined at anchoring apex 44. A first set of struts 46 are joined to each other along the axis for part of their length to form central stem 48 which extends from anchoring apex 44 to common joint 32 with diverging filter-wires. From this region struts 46 diverge in a parallel relation to struts 50. The divergence of the struts from the central axis is much steeper than the divergence of the filter-wires and the struts are much shorter. Both struts 46 and 50 have generally "s" shaped curved portions. An outer integral extension of struts 50 then turns and straightens to run parallel to the axis to joint 52 with the outer ends of respective struts 46. The straight portions of struts 50 are parallel to the vena cava wall, exposed for linear engagement with the wall with the ends of struts 46 and 50 pointing in the same direction as the ends of filter-wires 30. The struts overlap the filter-wires to a limited extent. Pointed projections 40 are disposed on the linear portions of strut 50 for engagement with the vena cava wall. Struts 46 and 50 thus form a stable "parallelogram" shape in the anchoring assembly. Filter-wires 30 joined to first set of struts 46 at common apex 32 are of helical form similar to the other described embodiments.

In FIG. 5 the parallel extension 50a of strut 50 is shown to be in linear contact with the vena cava wall. The contact between vena cava wall 42 and the parallel extension 50a of strut 50 is preserved in the case of smaller diameter vena cava shown in FIG. 5b, due to the action of the parallelogram supports when the assembly is compressed. Although the anchoring portion 28 is compressed in the small diameter case, it merely increases the overlap with the filter-wires and the overall length of the filter unit remains basically unchanged.

In alternative embodiments, shown in FIGS. 6 and 7, wall-engaging bars 54 are disposed on the ends of struts 38. The linear contact of bars 54 with the vessel wall provides stability to the filter unit 10 and assures that the filter will be self-centered once placed within vena cava 12. Preferable cross-sectional dimensions for bars 54 fall within the ranges given for struts 38.

Preferably, strut 38 and pointed projection 40 are attached to the bar 54 on opposite sides in the same vicinity so that the radial force from the strut is imparted directly on the pointed projection, causing it to securely lodge in vena cava wall 42. Preferably these points of attachment are in the mid-region of bar 54.

Figure 8:
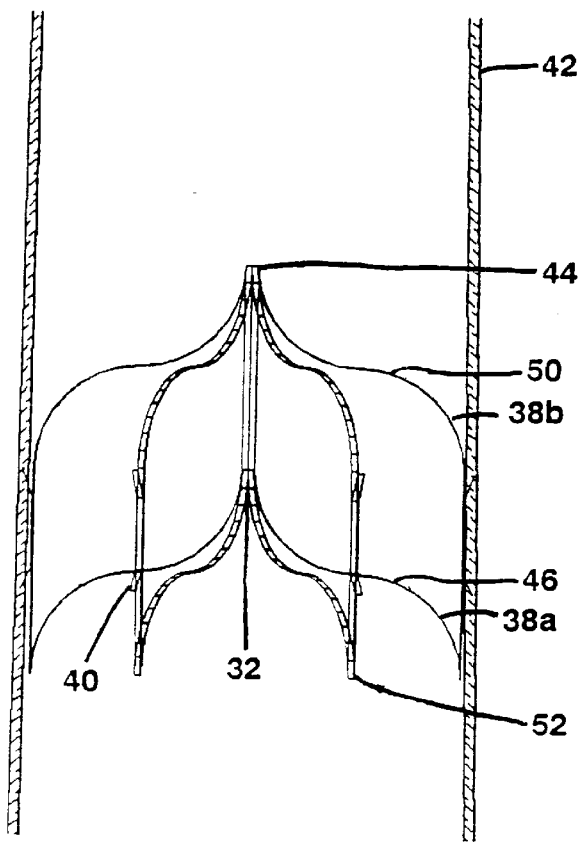
Figure 8B:
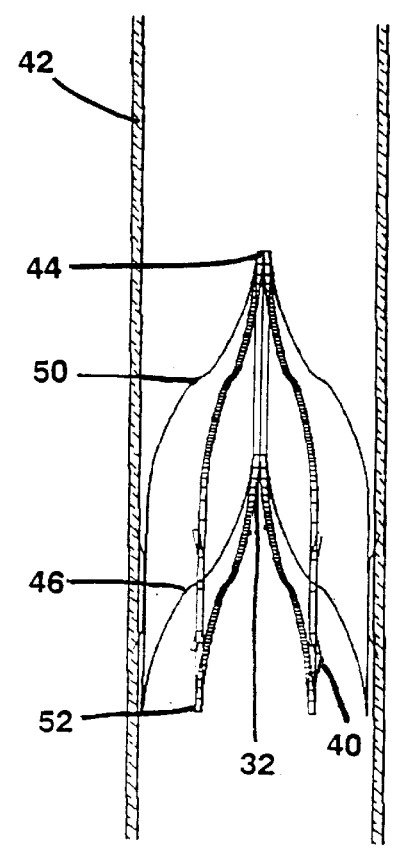
Figure 8A:
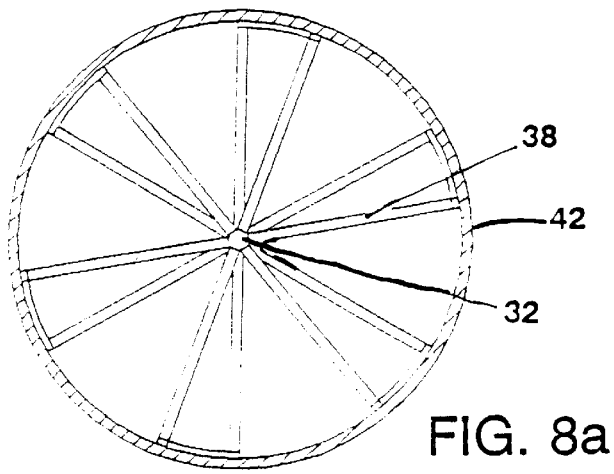
Figure 8C:
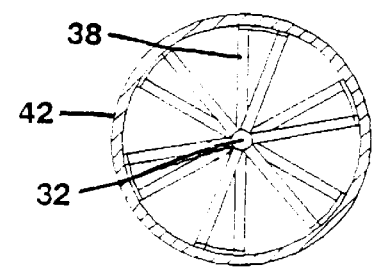

As shown in FIGS. 8 and 8b, the anchoring portion of FIG. 5 may be used alone as a vena cava filter. Because struts 46 and 50 are not helical, the number of struts in each set can be increased from what is shown to ensure adequate clot capturability. The view of the anchoring portion in the direction of the longitudinal axis of the vena cava is shown for the large (FIG. 8a) and small (FIG. 8c) diameter cases. As can be seen, the struts of the two sets are circumferentially offset from one another in this embodiment to increase the clot capture aspect presented to the blood stream.

Referring now to FIGS. 11–24, pointed projections are preferably placed on anchoring portion 28 to engage vena cava wall 42. For the filters shown in FIGS. 2–4, the vena cava wall contacting region is the end of the strut 38. In filters employing the "parallelogram" shaped double attached strut construction (FIGS. 5 and 8), or the bar-type strut construction (FIGS. 6 and 7), the pointed projection is preferably centrally located on the parallel strut extension 50a or bar 54. Various types of pointed projections may be used to anchor the vena cava filter, however, the pointed projection should be of limited length to avoid complete penetration of the vena cava walls.

FIGS. 11–24 show pairs of front and side views of the wall contacting region "A" of anchoring portion 28 which are of magnified scale to illustrate the position of the hooks. As shown in FIGS. 11–14, 19–22, a pointed projection is formed by cutting a strip of metal (or other suitable material) partially from the edge of the wall contacting element "A" while allowing it to remain integral at one end, and permanently bending it upward and inward. Pointed projections made in this fashion, pointing in either direction, are formed in either edge of the wall contacting element.

Alternatively, as shown in FIGS. 15 and 16, the wall contacting element "A" may be slit in two places and a separate piece woven into the slits to form hook 40.

Another method of forming a pointed projection is by sharpening the end of strut 38 or bar 54 and bending it back upon itself, as shown in FIGS. 17 and 18. If the tip is bent slightly outward, a stable and reliable hook may be formed. Still another method is to bond a parallel portion of separate hook form member face-wise to a wall contacting element "A" as shown in FIGS. 23 and 24.

It is preferable for the projections to point in both directions, as shown in FIGS. 11–16, 23 and 24. Vena cava filters should offer resistance to migration in either direction within the vena cava. Projections pointing in both directions may provide better protection against migration for this effect. Individual projections on adjacent struts may be oriented to point in opposite directions, or pairs of projections extending in opposite directions may be employed.

Still other embodiments are within the following claims.

What is claimed is:

1. A vascular filter for placement in a blood vessel for preventing the movement of emboli in the blood stream of a human, the filter comprising:
a set of filter-wires that diverge from a central joining region forming an emoboli-capturing array, the filter-wires having portions that engage the vessel wall; and
an anchoring assembly defined by at least one set of struts joined centrally with said set of filter-wires, wall engaging portions of said anchoring assembly constructed and arranged to engage the wall of said blood vessel in a manner anchoring said filter in position, the region of said anchoring being spaced from the region of contact of said set of filter wires with said vessel wall, wherein the struts extend from said central joining region a distance that is shorter than the distance said filter-wires extend from the central joining region, and diverge at a greater angle relative to the longitudinal axis of the filter than said filter-wires, the spacing of the regions of contact of said filter-wires and said struts with the vascular wall being selected to stabilize said filter in said vessel in a generally centered relationship.

2. The filter of claim 1, wherein said regions of contact of said set of filter-wires and of said set of struts are circumferentially offset from each other.

3. The filter of claim 1, wherein said struts diverge from said central joining region in the same general direction as said filter-wires diverge from said central joining region.

4. The filter of claim 1, wherein said struts diverge from said central joining region in a direction opposite the direction said filter-wires diverge from said central joining region.

5. The filter of claim 1, wherein said regions of contact of said filter-wires are upstream with respect to a direction of blood flow from said regions of contact of said struts.

6. The filter of claim 1, wherein said filter-wires have a continuous curvature when implanted.

7. The filter of claim 6, wherein said curvature of said filter-wires is generally concave facing the longitudinal axis.

8. The filter of claim 6, wherein said curvature of said filter-wires includes a generally helical mid-portion.

9. The filter of claim 1, wherein said struts have a continuous curvature when implanted.

10. The filter of claim 9, wherein said curvature of said struts is generally concave facing the longitudinal axis.

11. The filter of claim 10, wherein said filter-wires have a continuous curvature when implanted that is generally concave facing the longitudinal axis.

12. A vascular filter for placement in a blood vessel for preventing the movement of emboli in the blood stream of a human, the filter comprising:
an emboli-capturing portion having a set of filter-wires that diverge from a central joining region in a given direction along the blood vessel, the filter-wires terminating in free ends constructed to contact the wall of said vessel, wherein at least a portion of said filter-wires are of generally concave curved form with respect to a longitudinal axis of said filter and conform generally to an imaginary cone, and wherein said filter-wires are cooperatively related to form an effective emboli-capturing array.

13. The filter of claim 12, further comprising an anchoring assembly defined by least one set of struts diverging from said central joining region, portions of said anchoring assembly constructed to engage the wall of said blood vessel in a manner anchoring said filter in position, wherein the region of said anchoring is spaced from the region of contact of said filter-wires with said vessel wall.

14. The filter of claim 13, wherein the region of anchoring is upstream from the region of contact of said filter-wires with respect to a direction of blood flow in the vessel.

15. The filter of claim 13, wherein said struts extend from said central joining region a distance that is shorter than the distance said filter-wires extend from the central joining region, and diverge at a greater angle relative to the longitudinal axis of the filter than said filter-wires.

16. The filter of claim 13, wherein a mid-portion of said struts have a continuous curvature when implanted, wherein said curvature of said struts is generally concave with respect to a longitudinal axis of said filter.

17. The filter of claim 13, wherein said struts diverge from said central joining region in the same general direction as said filter-wires diverge from said central joining region.

18. The filter of claim 13, wherein said struts diverge from said central joining region in a direction opposite the direction said filter-wires diverge from said central joining region.

19. The filter of claim 12, wherein said mid-portion of said free ended filter-wires further have a helical curvature.

20. A vascular filter for placement in a blood vessel for preventing the movement of emboli in the blood stream of a human, the filter comprising:
an emboli-capturing portion having a set of filter-wires that diverge from a central joining region in a given direction along the blood vessel, the filter-wires terminating in free ends constructed to contact the wall of said vessel, wherein at least a mid-portion of said filter-wires are of generally curved form and conform generally to an imaginary cone, and wherein said filter-wires are cooperatively related to form an effective emboli-capturing array; and an anchoring assembly defined by at least one set of struts diverging from said central joining region, said anchoring assembly constructed to engage the wall of said blood vessel in a manner anchoring said filter in position, wherein the region of said anchoring is spaced upstream from the region of contact of said filter-wires with said vessel wall with respect to a direction of blood flow in the vessel.

21. The filter of claim 20, wherein a mid-portion of said struts have a continuous curvature when implanted.

22. The filter of claim 21, wherein said cuvature of said struts is generally concave with respect to a longitudinal axis of said filter.

23. A vascular filter for placement in a blood vessel for preventing the movement of emboli in the blood stream of a human, the filter comprising:

a set of filter-wires that diverge from a central region in a given direction along the blood vessel forming an emboli-capturing array, the filter-wires having portions that engage the vessel wall; and an anchoring assembly defined by at least one set of struts diverging from said central region in a direction opposite to the direction of divergence of said set of filter wires, the region of said anchoring being spaced from the region of contact of said set of filter-wires with said vessel wall, wherein said struts terminate in portions that engage the wall of said blood vessel in a manner anchoring said filter in position, the spacing of the regions of contact of said sets of filter-wires and said struts with the vascular wall being selected to stabilize said filter in said vessel in a generally centered relationship.

24. The filter of claim 23, wherein wall-engaging formations supported by said struts are constructed and arranged to maintain generally linear contact with the vessel walls.

25. The filter of claim 24, wherein said wall-engaging formations are linear elements each supported in its mid-region by a strut of said set.

26. The filter of claim 1, wherein said wall-engaging portions comprise linear elements constructed and arranged to maintain generally linear contact with the vessel walls, said linear elements each supported in its mid-region by a strut of said set.

27. A vascular filter for placement in a blood vessel for preventing the movement of emboli in the blood stream of a human, the filter comprising:

a set of filter-wires that diverge from a central region in a given direction along the blood vessel forming an emboli-capturing array, the filter wires having portions that engage the vessel wall; and an anchoring assembly defined by at least one set of struts joined centrally with said set of filter-wires, portions of said anchoring assembly contructed and arranged to engage the wall of said blood vessel in a manner anchoring said filter in position, the region of said anchoring being spaced from the region of contact of said set of filter-wires with said vessel wall, wherein said struts have free end portions constructed to engage the wall of said vessel, there being a plurality of anchoring formations on said strut, said formations arranged so that one said formation is relatively more effective for anchoring in walls of blood vessels of relatively large size and the other formation is relatively more effective for anchoring in walls of smaller size vessels.

28. The filter of claim 27, wherein each said anchoring formation comprises at least one pointed projection.

29. The filter of claim 27, wherein each said anchoring formation comprises at least one pair of pointed projections, the projections of said pair being oriented in opposite directions along the blood vessel, each being angled to penetrate into wall tissue, said pair of projections being effective to resist dislodgement of said strut in either direction along said vessel.

* * * * *

UNITED STATES PATENT AND TRADEMARK OFFICE
CERTIFICATE OF CORRECTION

PATENT NO. : 6,126,673
DATED : October 3, 2000
INVENTOR(S) : Kim, et al.

It is certified that error appears in the above-identified patent and that said Letters Patent is hereby corrected as shown below:

<u>Column 5,</u>
Line 12, the printed patent incorrecly reads "The parallelogram supports themselves form at least part", the patent should read -- The parallelogram support themselves from at least part --.
Line 62, the printed patent incorrectly reads "vena cave filter 10", the patent should read -- vena cava filter 10 --.

Signed and Sealed this

Thirtieth Day of October, 2001

Attest:

NICHOLAS P. GODICI
Attesting Officer     *Acting Director of the United States Patent and Trademark Office*

UNITED STATES PATENT AND TRADEMARK OFFICE
CERTIFICATE OF CORRECTION

PATENT NO. : 6,126,673
DATED : October 3, 2000
INVENTOR(S) : Kim et al.

It is certified that error appears in the above-identified patent and that said Letters Patent is hereby corrected as shown below:

Column 5,
Line 12, the printed patent incorrecly reads "The parallelogram supports themselves from at least part", the patent should read -- The parallelogram support themselves form at least part --.
Line 62, the printed patent incorrectly reads "vena cave filter 10", the patent should read -- vena cava filter 10 --.

This certificate supersedes Certificate of Correction issued October 30, 2001

Signed and Sealed this

Twentieth Day of August, 2002

Attest:

Attesting Officer

JAMES E. ROGAN
Director of the United States Patent and Trademark Office